US012589017B2

(12) United States Patent
Lee

(10) Patent No.: US 12,589,017 B2
(45) Date of Patent: Mar. 31, 2026

(54) ADJUSTABLE BODY BRACE AND ADJUSTING ASSEMBLY THEREOF

(71) Applicant: E-LIFE INTERNATIONAL CO., LTD., New Taipei City (TW)

(72) Inventor: Shih-Hsiang Lee, New Taipei City (TW)

(73) Assignee: E-Life International Co., Ltd., New Taipei City (TW)

( * ) Notice: Subject to any disclaimer, the term of this patent is extended or adjusted under 35 U.S.C. 154(b) by 241 days.

(21) Appl. No.: 18/479,508

(22) Filed: Oct. 2, 2023

(65) Prior Publication Data

US 2025/0107914 A1 Apr. 3, 2025

(51) Int. Cl.
*A61F 5/02* (2006.01)
(52) U.S. Cl.
CPC .................................... *A61F 5/022* (2013.01)
(58) Field of Classification Search
CPC .... A61F 5/0123; A61F 5/0125; A61F 5/0127; A61F 5/013; A61F 5/0102; A61F 5/0104; A61F 5/0106; A61F 5/0111; A61F 5/0113; A61F 2005/0146; A61F 2005/0158; A61F 5/022; A61F 5/024; A61F 5/026; A61F 5/028; E05B 15/0046; E05B 15/0053; E05B 15/006; E05B 1/0007; E05B 1/0038; E05B 1/0046
See application file for complete search history.

(56) References Cited

U.S. PATENT DOCUMENTS

| | | | | |
|---|---|---|---|---|
| 6,821,261 | B2 * | 11/2004 | Doty ..................... | A61F 5/0125 602/5 |
| 6,827,653 | B2 * | 12/2004 | Be ........................ | A63B 71/148 2/161.1 |
| 9,925,082 | B2 * | 3/2018 | Chetlapalli ........... | A61F 5/0123 |
| 11,969,376 | B2 * | 4/2024 | Dellanno .................. | A61F 5/32 |
| 2002/0183672 | A1 * | 12/2002 | Enzerink .............. | A61F 5/0125 602/26 |
| 2006/0155229 | A1 * | 7/2006 | Ceriani ................. | A61F 5/0125 602/5 |
| 2011/0009786 | A1 * | 1/2011 | Chan ..................... | A61F 5/0125 602/16 |
| 2011/0105971 | A1 * | 5/2011 | Ingimundarson ....... | A61F 5/028 602/19 |
| 2014/0100501 | A1 * | 4/2014 | Burke ..................... | A61F 5/026 602/19 |

(Continued)

*Primary Examiner* — Kari K Rodriquez
(74) *Attorney, Agent, or Firm* — Best & Flanagan LLP

(57) ABSTRACT

An adjustable body brace includes an adjusting assembly and two board units. The adjusting assembly includes a base, a slider, and a fixing module. The base has a limit groove and two wall surfaces. The limit groove extends along a length direction; two wall surfaces are located at two opposite lateral sides of the limit groove. The slider is movably mounted on the base. The fixing module is connected to the slider, and includes an engaging unit. The engaging unit has an engaging portion which is selectively located in the limit groove and engages with the two wall surfaces to fix a position of the slider with respect to the base. The two board units are respectively connected to the base and the slider. With the engaging unit engaged in different positions of the limit groove, the position of the slider with respect to the base is adjustable.

4 Claims, 14 Drawing Sheets

(56)                    References Cited

U.S. PATENT DOCUMENTS

| | | | | |
|---|---|---|---|---|
| 2014/0364782 A1* | 12/2014 | Knecht | ................ | A61F 5/0125 |
| | | | | 602/16 |
| 2016/0045387 A1* | 2/2016 | Lee | ....................... | A61H 3/008 |
| | | | | 602/12 |
| 2022/0280324 A1* | 9/2022 | Romo | ..................... | A61F 5/024 |

* cited by examiner

ADJUSTABLE BODY BRACE AND ADJUSTING ASSEMBLY THEREOF

BACKGROUND OF THE INVENTION

1. Field of the Invention

The present invention relates to an adjustable body brace, especially to an adjustable body brace that is capable of adjusting a total length.

2. Description of the Prior Arts

Activities of human joints involve cooperation of bones and muscles, if support strength of the muscles is insufficient due to injuries or ageing, the joints may be harmed under over-stressed occasions and thus lead to pain or further harm to the body. To prevent compensation caused by inappropriate contraction or stretching of the muscles, a body brace is set to limit an activity range of the joint, and the body brace is also capable of supplying extra support to the body, thereby easing the pain of the body.

However, a conventional body brace is incapable of adjusting a total length, and thus the conventional body brace can only support at same positions around the joint, such that the conventional body brace fails to correspond to varied body sizes; on the other hand, due to varied body sizes of different people, for example, a length of a limb around the ankle or the knee may be largely different from person to person, and thus the positions for the body brace to support may be also largely different; therefore, an institution or facility of injury treatments such as a sport injury prevention and protection center or a school health center has to spend much to prepare body braces in different sizes for patients who are varied in body sizes.

Besides, the positions for the body brace to support of the same user May need alteration due to a disease progression or a change of an injury condition of the joint; however, the conventional body brace can only be set on the same positions, and therefore, the user has to purchase a new body brace, which causes inconvenience.

To overcome the shortcomings, the present invention provides an adjustable body brace to mitigate or obviate the aforementioned problems.

SUMMARY OF THE INVENTION

The main objective of the present invention is to provide an adjustable body brace that is capable of adjusting a total length of the adjustable body brace to fit varied body sizes of different users.

The adjustable body brace has an adjusting assembly and two board units. The adjusting assembly has a base, a slider, and a fixing module. The base has a length direction and a thickness direction, and the base includes a first surface, a limit groove, and two wall surfaces. The limit groove is recessed from the first surface along the thickness direction and extends along the length direction. The two wall surfaces are respectively located on two opposite lateral sides of the limit groove along the length direction. The slider is movably mounted on the base, and is movable with respect to the base along the length direction. The fixing module is connected to the slider and mounted in the limit groove, and the fixing module has a locked state and an unlocked state; the fixing module includes an engaging unit movable along the thickness direction. The engaging unit has an engaging portion selectively located in the limit groove. Wherein, when the fixing module is under the locked state, the engaging portion is in the limit groove and engages with the two wall surfaces, and thereby a position of the slider with respect to the base is fixed; when the fixing module is under the unlocked state, the engaging portion is out of the limit groove. The two board units are respectively connected to the base and the slider.

Therefore, with the engaging unit of the fixing module engaged in different positions of the limit groove, a position of the slider with respect to the base is adjustable, and thereby a distance between two board units as well as the total length of the adjustable body brace are adjustable to fit varied body sizes of different people. In addition, the fixing module is easy to be switched between the locked state and the unlocked state without complicated procedures, thereby being beneficial for the user to adjust the total length of the adjustable body brace rapidly.

Other objectives, advantages and novel features of the invention will become more apparent from the following detailed description when taken in conjunction with the accompanying drawings.

DETAILED DESCRIPTION OF THE PREFERRED EMBODIMENTS

For conciseness in description, embodiments of an adjustable body brace in this specification involve examples which fit a waist of a user, but it is not limited thereto; the adjustable body brace in this disclosure may have alternative embodiments which fit different body parts, such as elbows, knees, ankles, and so on.

Figure 1:
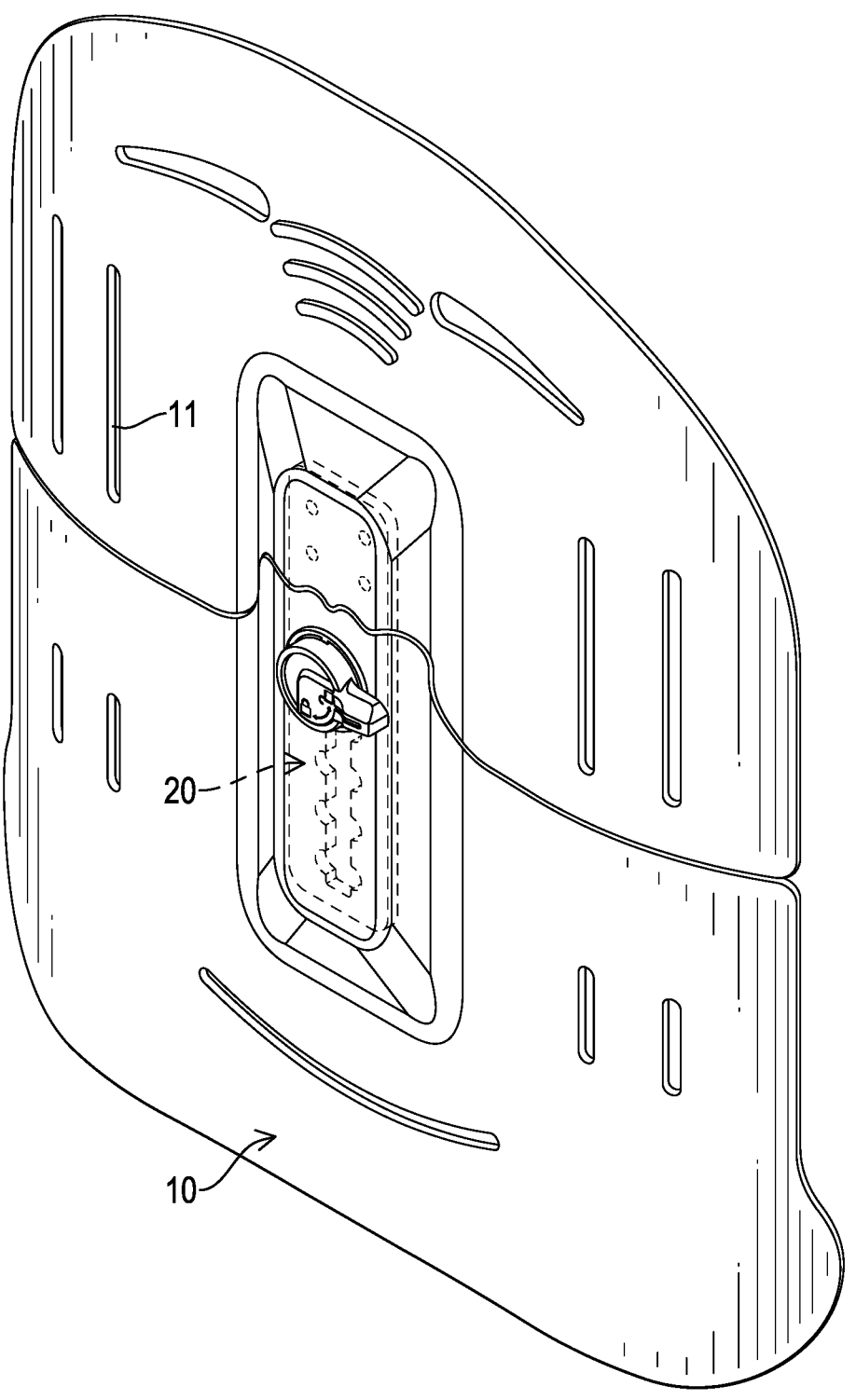
FIG. 1 is a perspective view of a first embodiment of an adjustable body brace in accordance with the present invention.
Figure 2:
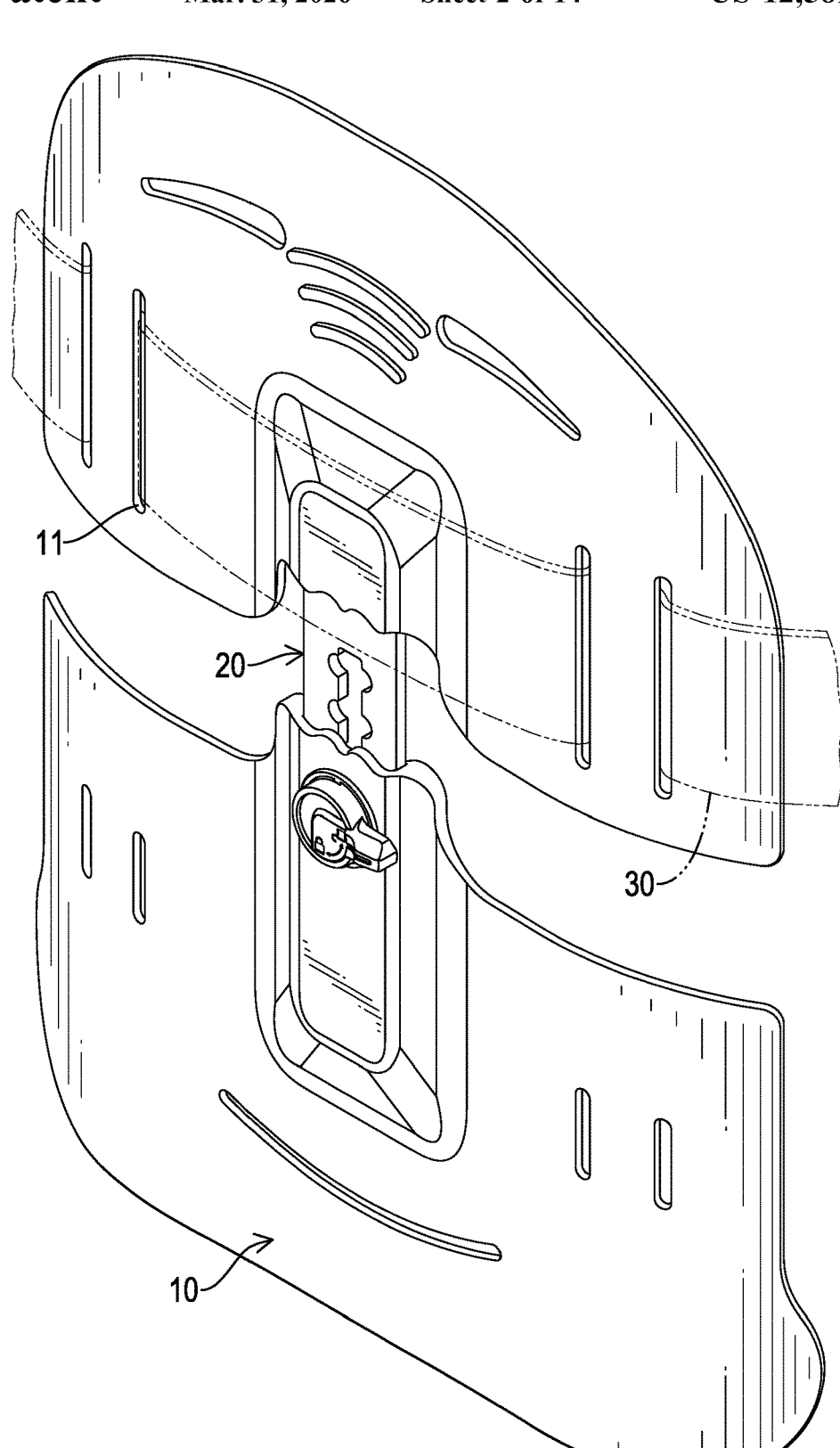
FIG. 2 is a perspective view of the adjustable body brace in FIG. 1, shown length adjusted.
Figure 3:
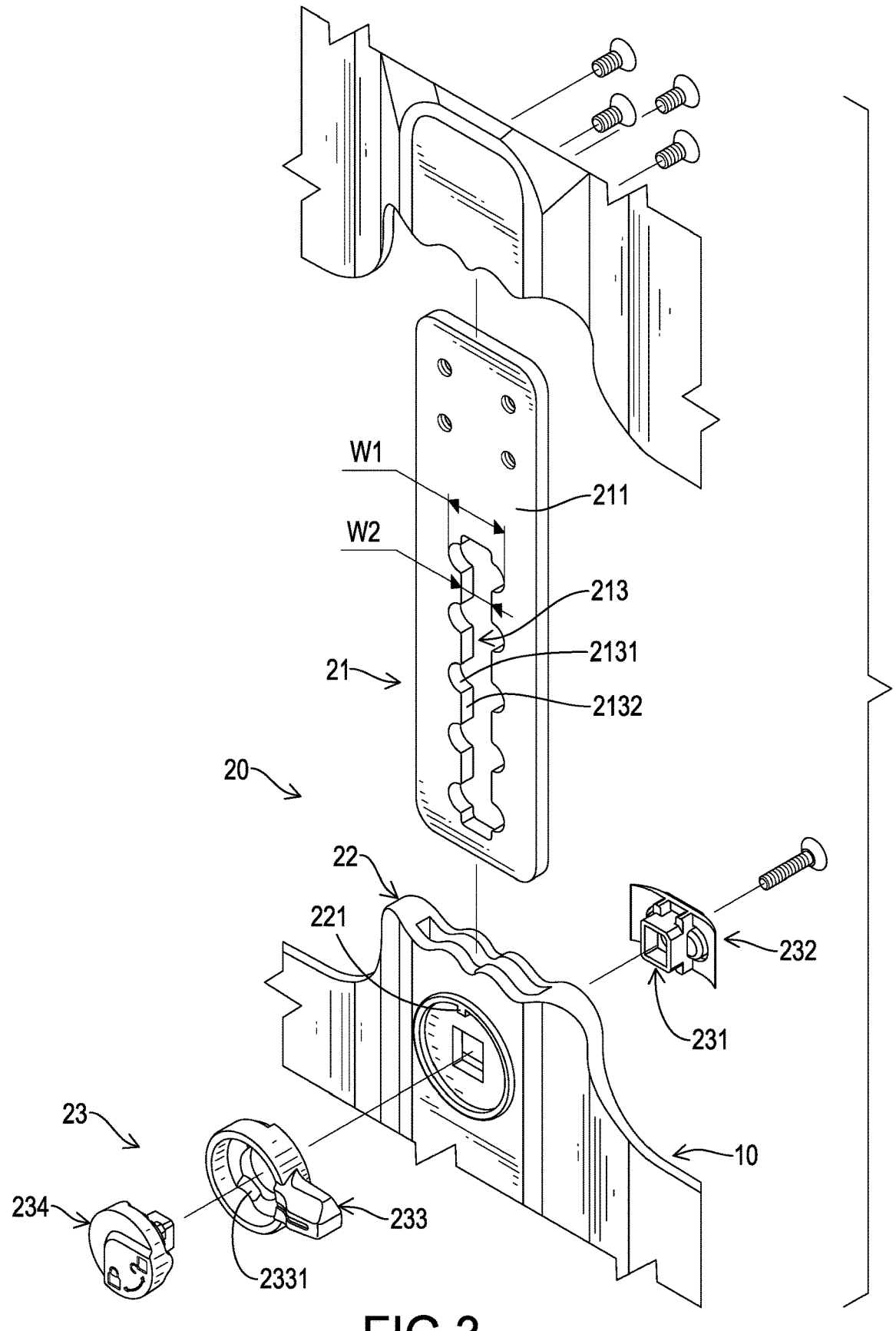
FIG. 3 is a partial exploded view of the adjustable body brace in FIG. 1.
Figure 4:
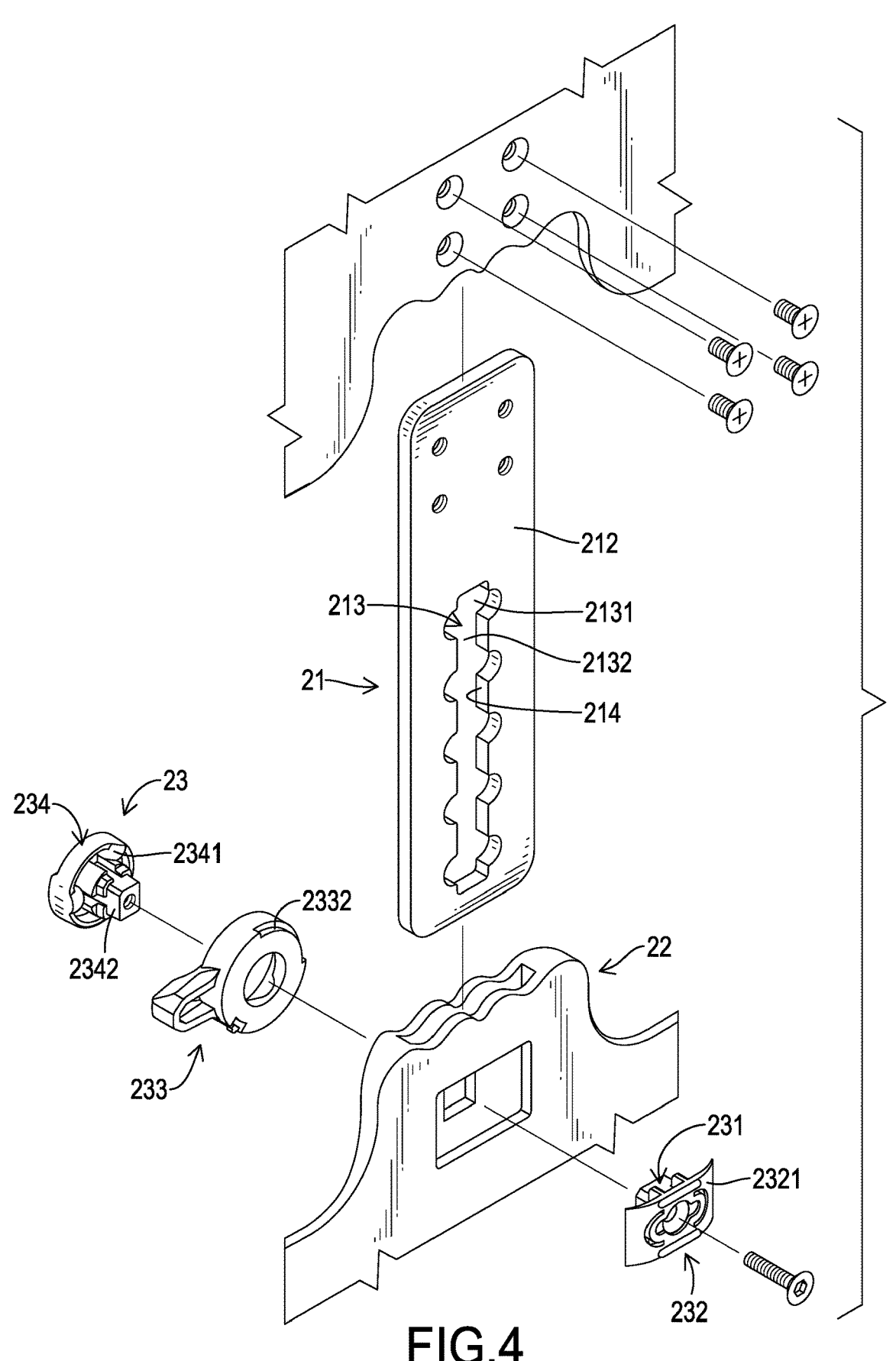
FIG. 4 is the adjustable body brace in FIG. 3 viewed from another angle.

With reference to FIGS. 1 to 3, a first embodiment of the adjustable body brace in accordance with the present invention includes two board units 10 and an adjusting assembly 20.

Each one of the board units 10 is connected to the adjusting assembly 20, the board unit 10 in this embodiment fits a waist part of a user, but it is not limited thereto, the board unit 10 may be altered for fitting different body parts of a person such as elbows or knees. In this embodiment, each one of the board units 10 may have multiple penetrating holes 11, the penetrating holes 11 are formed through the board unit 10; the adjustable body brace may further have multiple belts 30, the belts 30 are mounted through the penetrating holes 11, and thereby the user is able to fix the adjustable body brace to a body of the user, but it is not limited thereto; in another embodiment, the board units 10 may not have the penetrating holes 11, and/or the adjustable body brace may not have the belts 30, and the adjustable body brace is fixed to the body of the user via another method.

The adjusting assembly 20 is configured to adjust a total length of the adjustable body brace in this disclosure; to be more precise, the adjusting assembly 20 is capable of being installed on a body brace which has two board units being separate from each other.

With reference to FIGS. 2 to 5, the adjusting assembly 20 includes a base 21, a slider 22, and a fixing module 23. The two board units 10 are respectively connected to the base 21 and the slider 22.

The base 21 has a length direction and a thickness direction, and the base 21 includes a first surface 211, a second surface 212, a limit groove 213, and two wall surfaces 214. The length direction and the thickness direction are perpendicular to each other. The second surface 212 is opposite to the first surface 211; to be more precise, the first surface 211 and the second surface 212 are two opposite surfaces of the base 21 along the thickness direction.

The limit groove 213 is recessed from the first surface 211 along the thickness direction, and extends along the length direction; in this embodiment, the limit groove 213 penetrates the second surface 212 along the thickness direction, but it is not limited thereto; in another embodiment, the limit groove 213 may not penetrate the second surface 212. The limit groove 213 has multiple limit segments 2131, the limit segments 2131 are disposed along the length direction and spaced apart from each other, and a connecting segment 2132 connects with each adjacent two of the limit segments 2131.

The two wall surfaces 214 are respectively located on two opposite lateral sides of the limit groove 213 along the length direction. A distance between the two wall surfaces 214 at each one of the limit segments 2131 is a first width W1, and another distance between the two wall surfaces 214 at each one of the connecting segments 2132 is a second width W2; the first width W1 is larger than the second width W2. In other words, the connecting segment 2132 is a neck of the adjacent two of the limit segments 2131.

The slider 22 is movably mounted on the base 21, to be more precise, the slider 22 is movable with respect to the base 21 along the length direction. In this embodiment, the slider 22 is integrally connected to the board unit 10, but it is not limited thereto; in another embodiment, the slider 22 may be connected to the board unit 10 via bolts.

The fixing module 23 has a locked state and an unlocked state. When the fixing module 23 is under the unlocked state, the slider 22 is capable of moving with respect to the base 21 along the length direction; when the fixing module 23 is under the locked state, a position of the slider 22 with respect to the base 21 is fixed, thereby the total length of the adjustable body brace being fixed.

The fixing module 23 is connected to the slider 22 and mounted through the limit groove 213; to be more precise, in this embodiment, the slider 22 is movably sleeved on the base 21, and the fixing module 23 is mounted through the slider 22 and the limit groove 213 of the base 21 simultaneously, but it is not limited thereto, a mounting method of the fixing module 23 on the slider 22 may be altered according to the requirements.

The fixing module 23 includes an engaging unit 231, an elastic unit 232, a knob 233, and an abutting unit 234. The engaging unit 231 is movable along the thickness direction, and the engaging unit 231 has an engaging portion 2311. The engaging portion 2311 is selectively located in the limit groove 213; to be more precise, when the fixing module 23 is under the locked state, the engaging unit 231 moves to the limit groove 213, and thus the engaging portion 2311 is located in the limit groove 213; when the fixing module 23 is under the unlocked state, the engaging unit 231 moves away from the limit groove 213, and thus the engaging portion 2311 is located out of the limit groove 213.

When the engaging portion 2311 is located in the limit groove 213, the engaging portion 2311 engages with the two wall surfaces 214, and thereby the position of the slider 22 with respect to the base 21 is fixed. To be more precise, the engaging portion 2311 of the engaging unit 231 is selectively mounted through the limit groove 213, and when the fixing module 23 is under locked state, the engaging portion 2311 is located in one of limit segments 2131 of the limit groove 213; because a width of the engaging portion 2311 is smaller than the first width W1 or approximately equal to the first width W1, and the width of the engaging portion 2311 is larger than the second width W2, the engaging portion 2311 is obstructed by the connecting segment 2132, and thereby the slider 22 is not capable of moving along the length direction.

The elastic unit 232 is connected to the engaging unit 231 and located out of the limit groove 213, and thereby the elastic unit 231 is capable of driving the engaging unit to move along the thickness direction; in this embodiment, the elastic unit 232 is integrally connected to an end of the engaging unit 231, and the elastic unit 232 has two wing portions 2321 which abut the second surface 212, thereby pulling the engaging unit 231 to move toward the second surface 212, but it is not limited thereto, in another embodiment, the elastic unit 232 may not be connected to the engaging unit 231 integrally.

The knob 233 is rotatably sleeved on the abutting unit 234 and abuts on the slider 22; the knob 233 has an oblique surface 2331 and an outer groove 2332. The oblique surface 2331 is located on a surface of the knob 233, and said surface is away from the slider 22, and the oblique surface 2331 is oblique along a rotating direction of the knob 233. The outer groove 2332 is recessed from an outer annular surface of the knob 233 and extends along a circumferential direction of the knob 233; to be more precise, the outer groove 2332 is a curved groove which is formed on and extends along the outer annular surface of the knob 233, and the outer groove 2332 has two opposite ends. As shown in FIG. 2, the slider 22 may further have a protrusion 221 located in the outer groove 2332; when the fixing module 23 is under the locked state or the unlocked state, the protrusion 221 is located at either one of the two opposite ends of the outer groove 2332, thereby limiting a range of a rotating angle of the knob 233.

The abutting unit 234 is connected to another end of the engaging unit 231, and said end is opposite to the end connected to the elastic unit 232; the abutting unit 234 is movable along the thickness direction; in this embodiment, the abutting unit 234 includes an abutting portion 2341 and a pole portion 2342, the pole portion 2342 is movably mounted through the limit groove 213 and connected to the engaging unit 231, and a width of the pole portion 2342 is smaller than the second width W2 of the limit groove 213, thereby the pole portion 2342 being capable of moving from one of the limit segments 2131 to another through the connecting segments 2132 in the limit groove 213; the abutting portion 2341 slidably abuts on the oblique surface 2331, and thereby when the knob 233 rotates, the oblique surface 2331 pushes the abutting unit 234 and drives the engaging unit 231 to move along the thickness direction.

Figure 5:
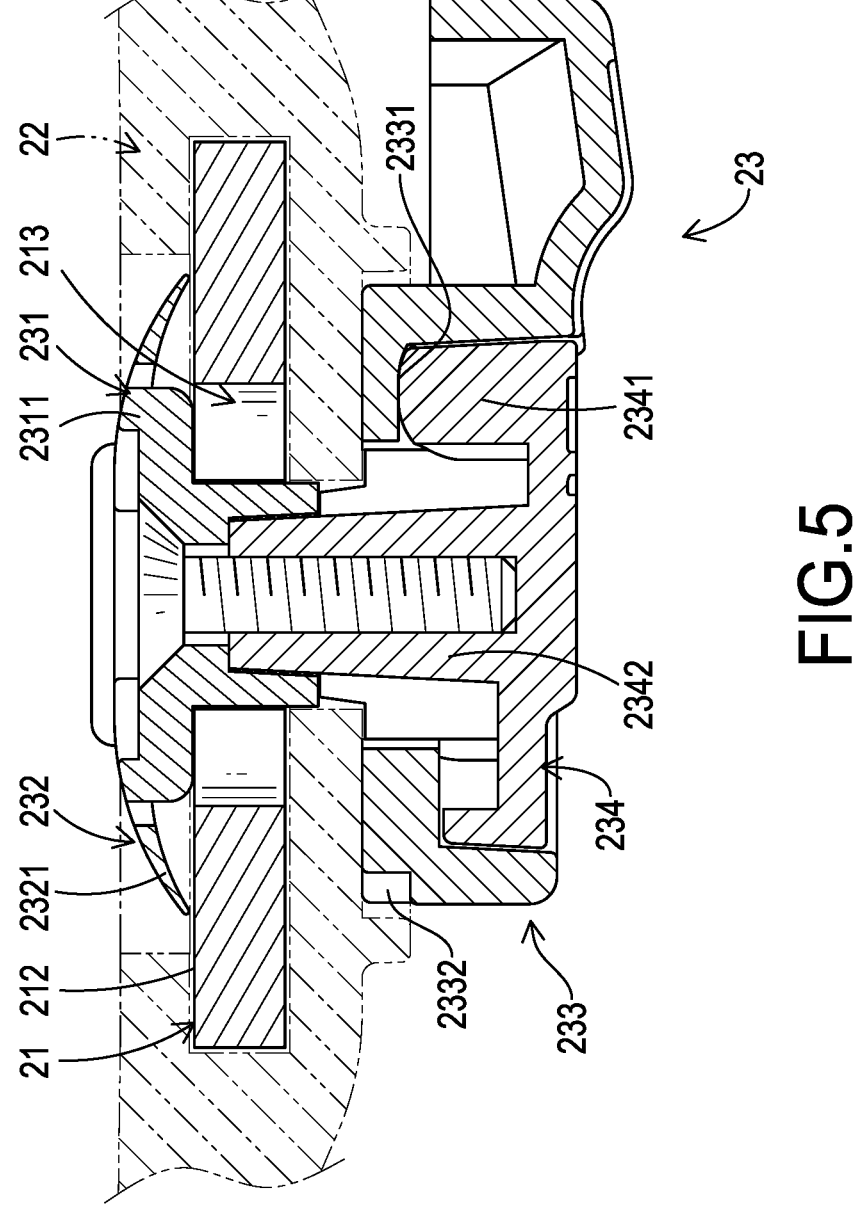
FIG. 5 is a cross-sectional view of the adjustable body brace in FIG. 1, showing a fixing module under an unlocked state.
Figure 6:
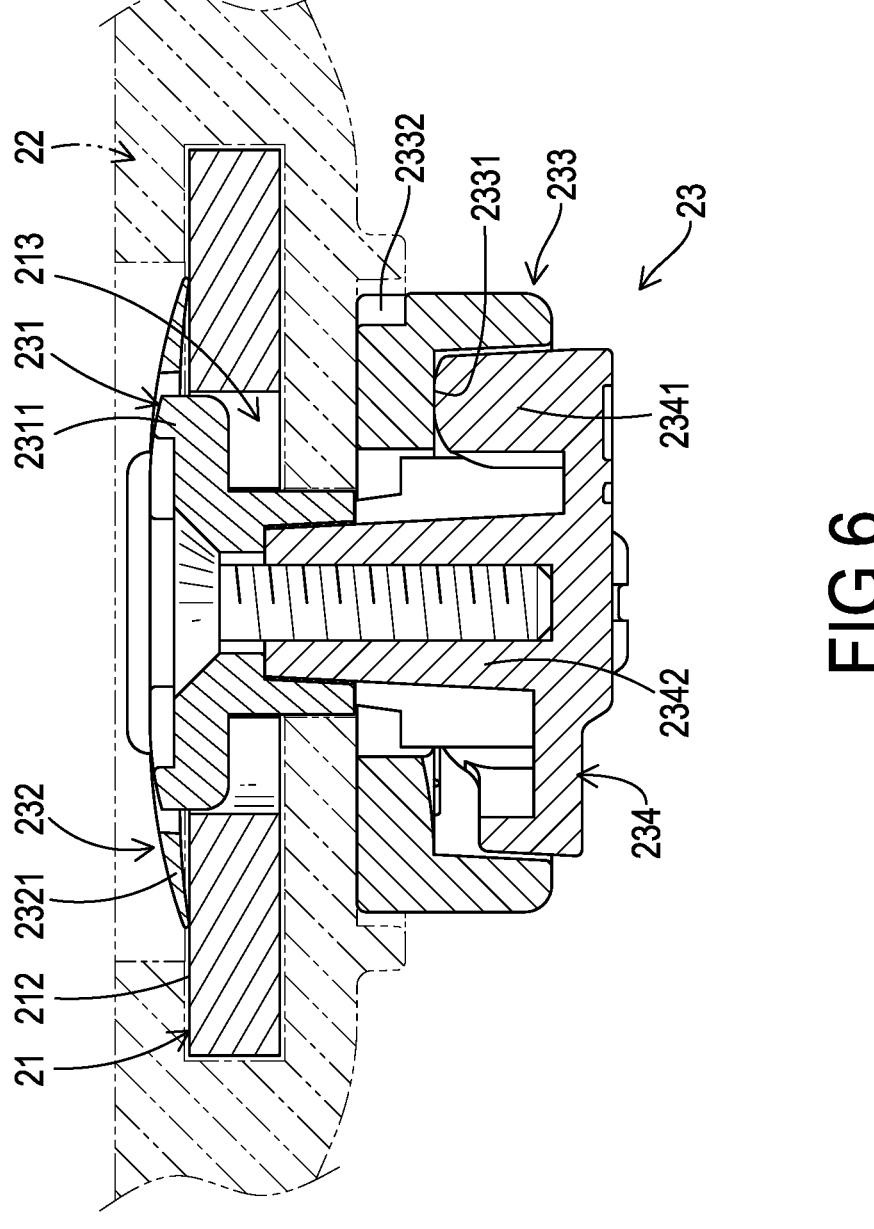
FIG. 6 is a cross-sectional view of the adjustable body brace in FIG. 1, showing the fixing module under a locked state.
Figure 7:
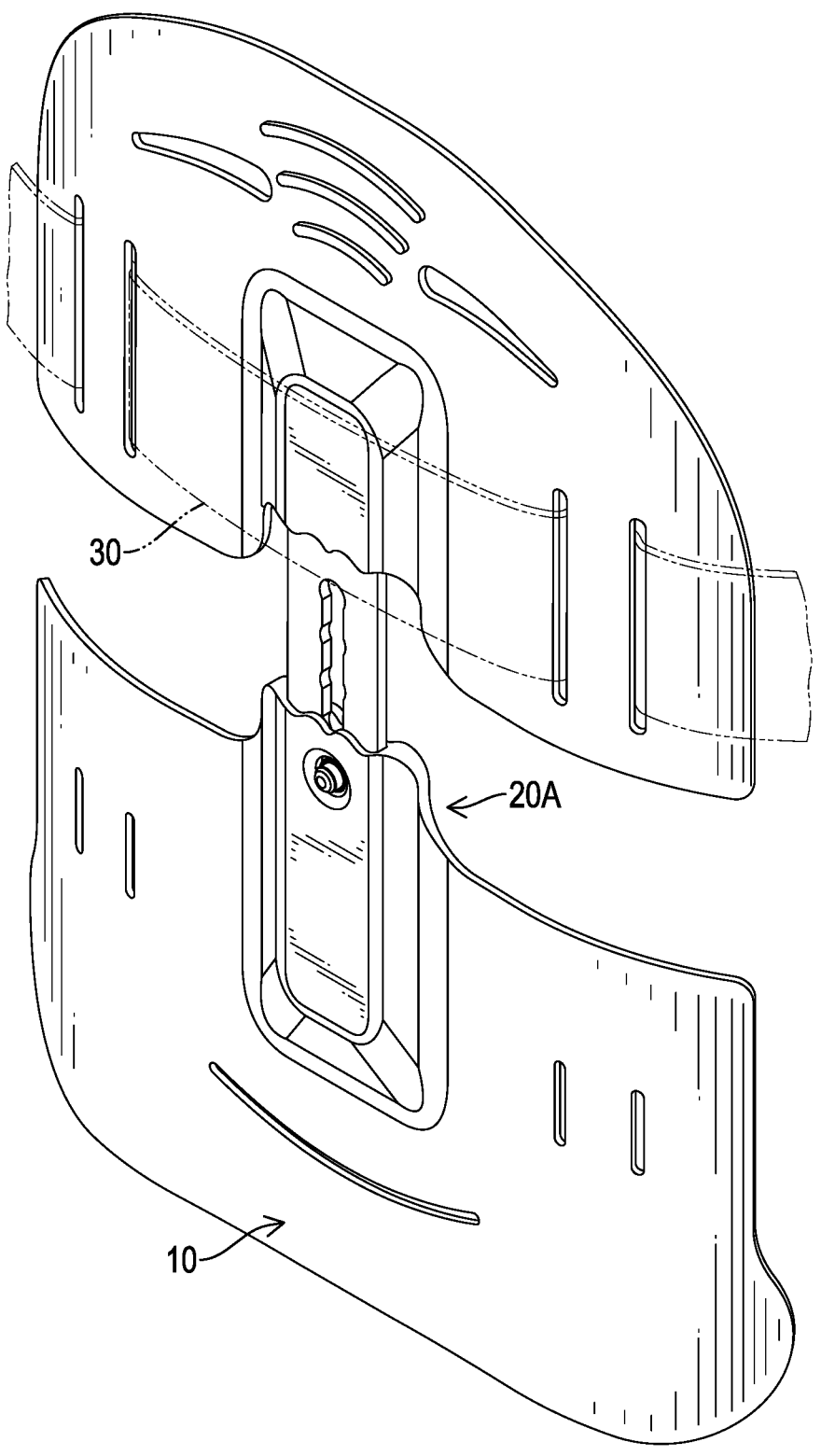
FIG. 7 is a perspective view of a second embodiment of the adjustable body brace in accordance with the present invention.
Figure 8:
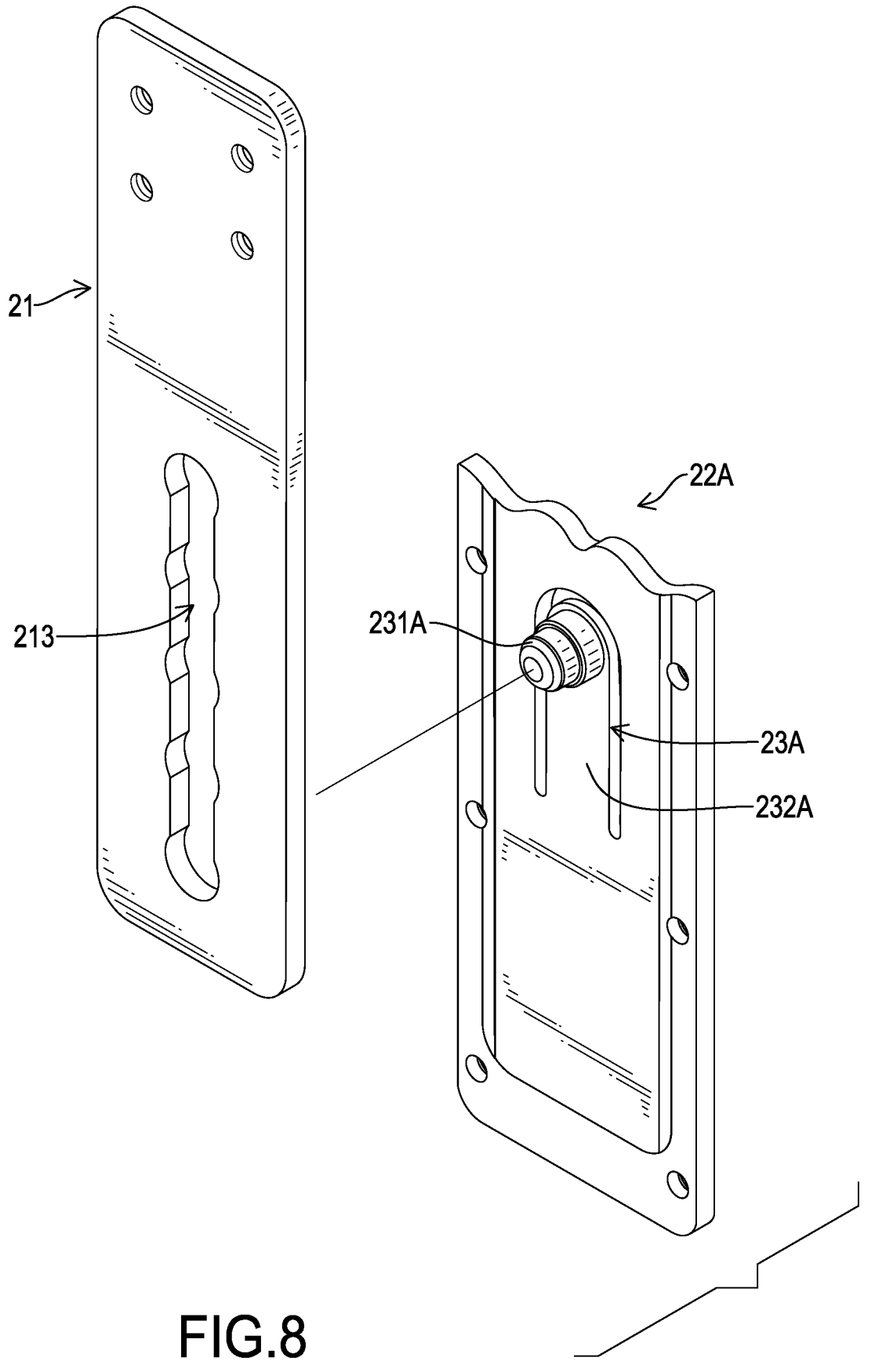
FIG. 8 is an exploded view of the adjustable body brace in FIG. 7.

Next, with reference to FIG. 5, when the fixing module 23 is under the unlocked state, the engaging portion 2311 is located out of the limit groove 213, such that the slider 22 is capable of moving with respect to the base 21 along the length direction; when the knob 233 as well as the oblique surface 2331 rotate, the abutting unit 234 is pressed to move along the thickness direction, driving the engaging unit 231 to move into the limit groove 213; thereby the fixing module 23 entering the locked state shown in FIG. 6, such that the slider 22 is not capable of moving with respect to the base 21 and thus fixing the position of the slider 22 with respect to the base 21.

The two wing portions 2321 of the elastic unit 232 abut the second surface 212 of the base 21, and have a tendency of stretching along a direction away from the second surface 212, and thereby the engaging unit 231 tends to move out from the limit groove 213. When the fixing module 23 is switched from the unlocked state to the locked state, the elastic unit 232 is deformed and accumulates elastic energy; on the contrary, when the knob 233 rotates for the fixing module 23 switching from the locked state to the unlocked state, the elastic unit 232 gradually stretches away from the second surface 212 and pulls the engaging unit 231 to leave the limit groove 213, and finally, the fixing module 23 returns to the unlocked state shown in FIG. 5.

Next, with reference to FIGS. 7 to 10, a second embodiment of the adjustable body brace is similar to the first embodiment, but a main difference between the first embodiment and the second embodiment is the fixing module 23A of the adjusting assembly 20A. In the second embodiment of the adjustable body brace, the fixing module 23A includes an engaging unit 231A and an elastic unit 232A. The elastic unit 232A is a bar and has two opposite ends. One of the two ends of the elastic unit 232A is connected to the engaging unit 231A, and another one of the two ends of the elastic unit 232A is connected to the slider 22A. The elastic unit 232A is bendable, and thereby the end connected to the engaging unit 231A of the elastic unit 232A is capable of moving with respect to another one of the ends of the elastic unit 232A along the thickness direction of the base 21. In addition, in this embodiment the elastic unit 232A may be integrally formed with the slider 22A, but it is not limited thereto.

Figure 9:
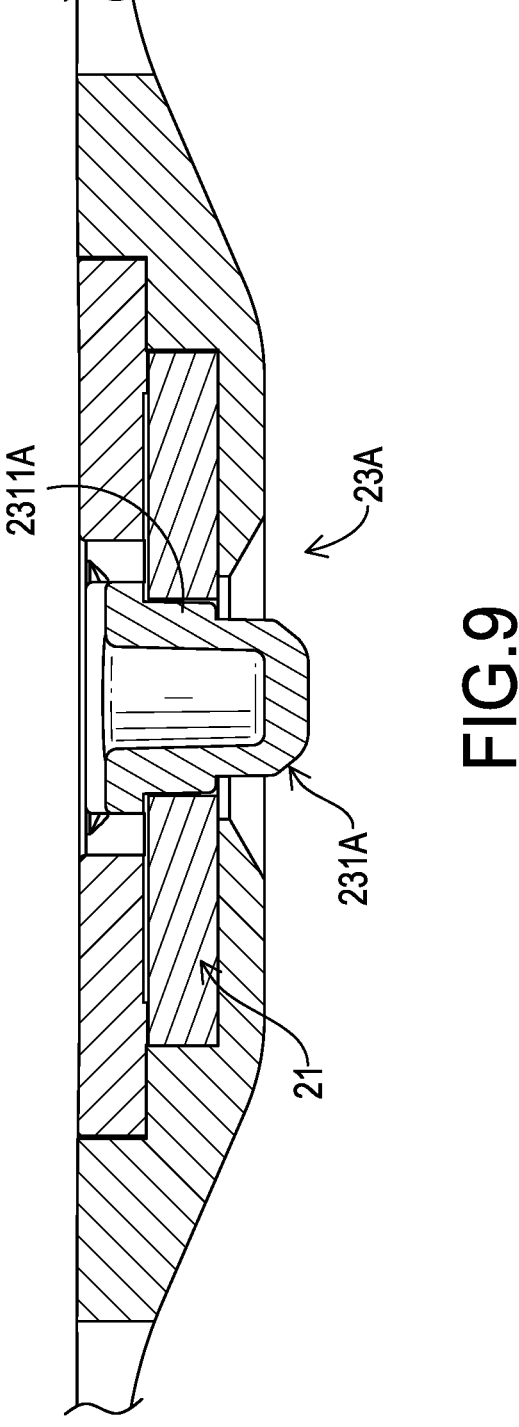
FIG. 9 is a cross-sectional view of the adjustable body brace in FIG. 7, showing the fixing module under the locked state.
Figure 10:
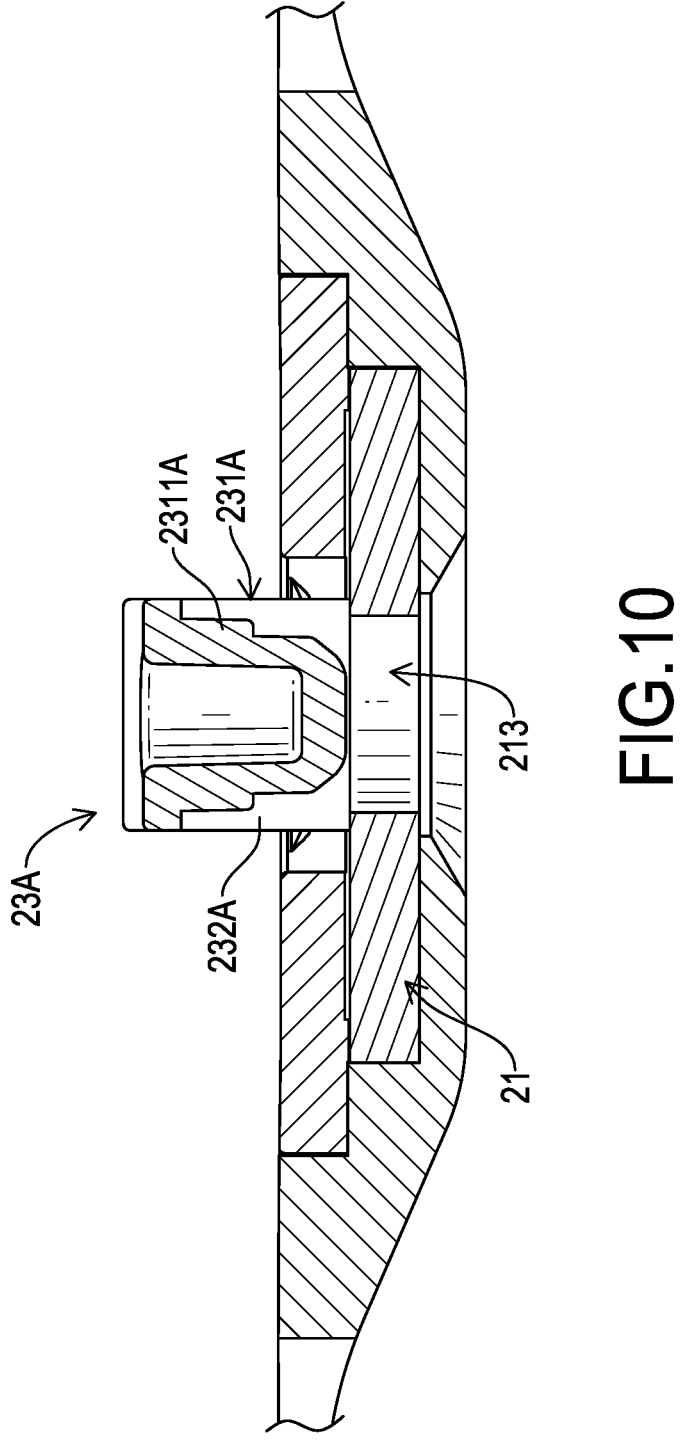
FIG. 10 is a cross-sectional view of the adjustable body brace in FIG. 7, shown the fixing module under the unlocked state.
Figure 11:
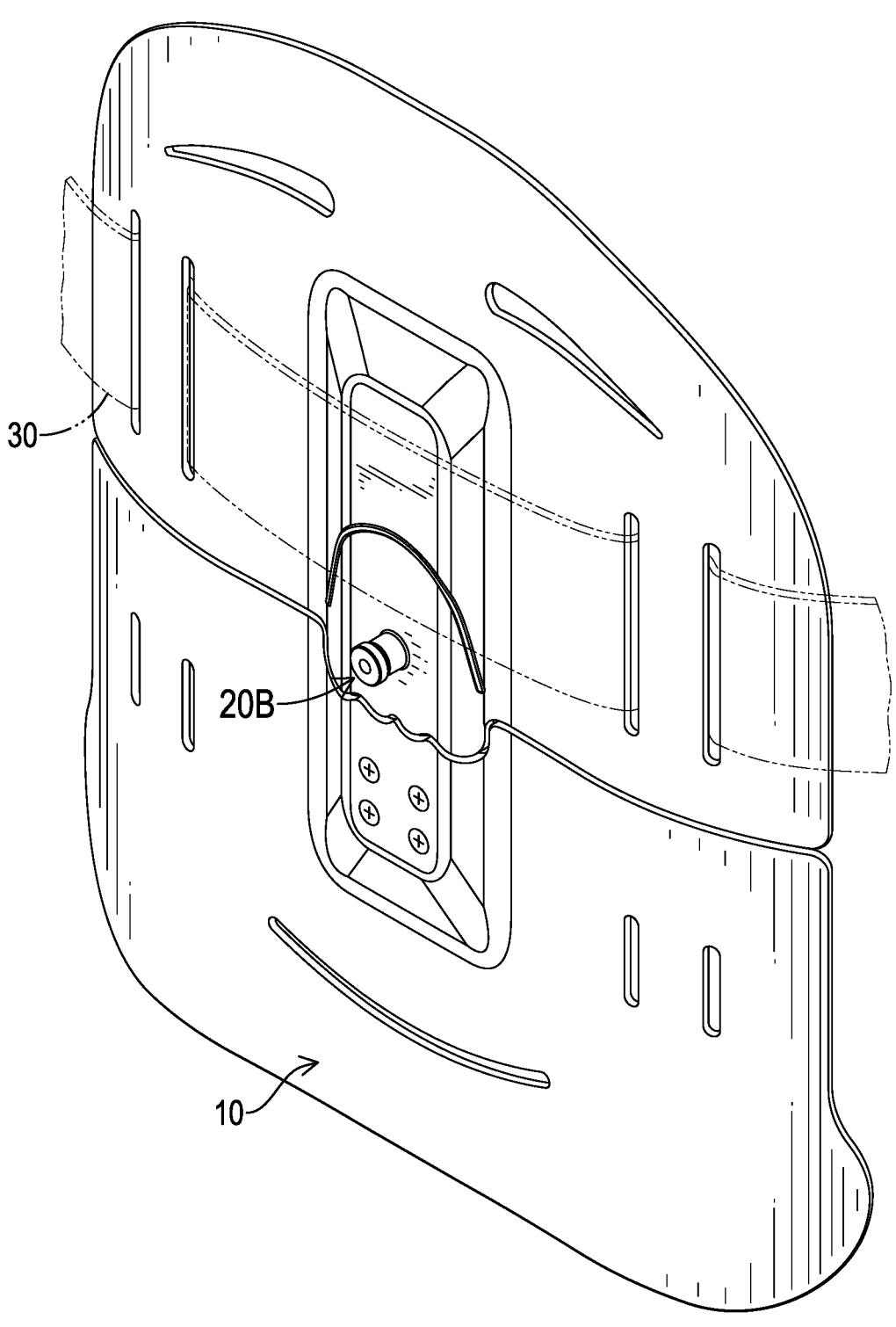
FIG. 11 is a perspective view of a third embodiment of the adjustable body brace in accordance with the present invention.
Figure 12:
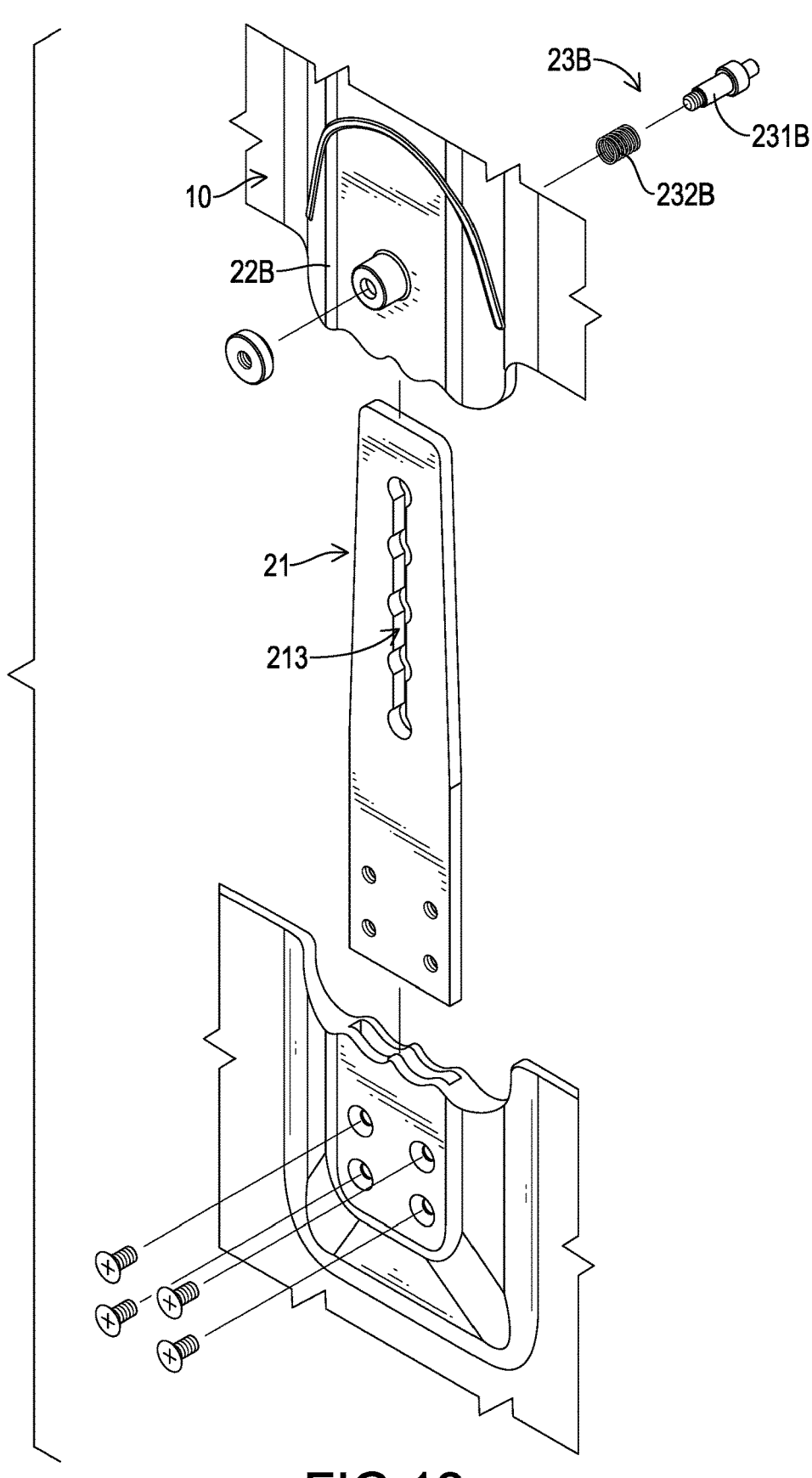
FIG. 12 is an exploded view of the adjustable body brace in FIG. 11.

To be more precise, the fixing module 23A in this embodiment is in a configuration of a button. As shown in FIG. 9, when the fixing module 23A is under the locked state, the engaging portion 2311A is located in the limit groove 213; when the engaging unit 231A is pressed to move along the thickness direction, the engaging portion 2311A leaves the limit groove 213, and the fixing module 23A is switched into the unlocked state as shown in FIG. 10, and the elastic unit 232A is deformed. When the engaging unit 231A is not pressed, the elastic unit 232A restores, such that the engaging portion 2311A moves back to the limit groove 213, and thus the fixing module 23A returns to the locked state.

Next, with reference to FIGS. 11 to 14, a third embodiment of the adjustable body brace is similar to the first embodiment, but a main difference between the first embodiment and the third embodiment is the slider 22B and the fixing module 23B of the adjusting assembly 20B. Besides, in this embodiment, the slider 22B is integrally formed with one of the board units 10, but it is not limited thereto. The fixing module 23B includes an engaging unit 231B and an elastic unit 232B, and the slider 22B further has a first abutting surface 222B. The first abutting surface 222B is located out of the limit groove 213 and faces to the limit groove 213 along the thickness direction of the base 21.

The engaging unit 231B further has a second abutting surface 2312B, and the second abutting surface 2312B faces to the first abutting surface 222B along the thickness direction of the base 21. To be more precise, the engaging unit 231B has an engaging portion 2311B, an extending portion 2313B, and a handle 2314B. The second abutting surface 2312B is a surface of the engaging portion 2311B, and said surface faces to the first abutting surface 222B; The extending portion 2313B connects with the engaging portion 2311B and the handle 2314B. The extending portion 2313B extends from the second abutting surface 2312B to the first abutting surface 222B of the slider 22B, and the extending portion 2313B penetrates through the first abutting surface 222B. The handle 2314B is located out of the slider 22B, and selectively abuts another surface of the slider 22B and said another surface is opposite to the first abutting surface 222B.

The elastic unit 232B is a compression spring, and the elastic unit 232B is sleeved on the extending portion 2313B of the engaging unit 231B, and two opposite ends of the elastic unit 232B respectively abut the first abutting surface 222B and the second abutting surface 2312B.

Figure 13:
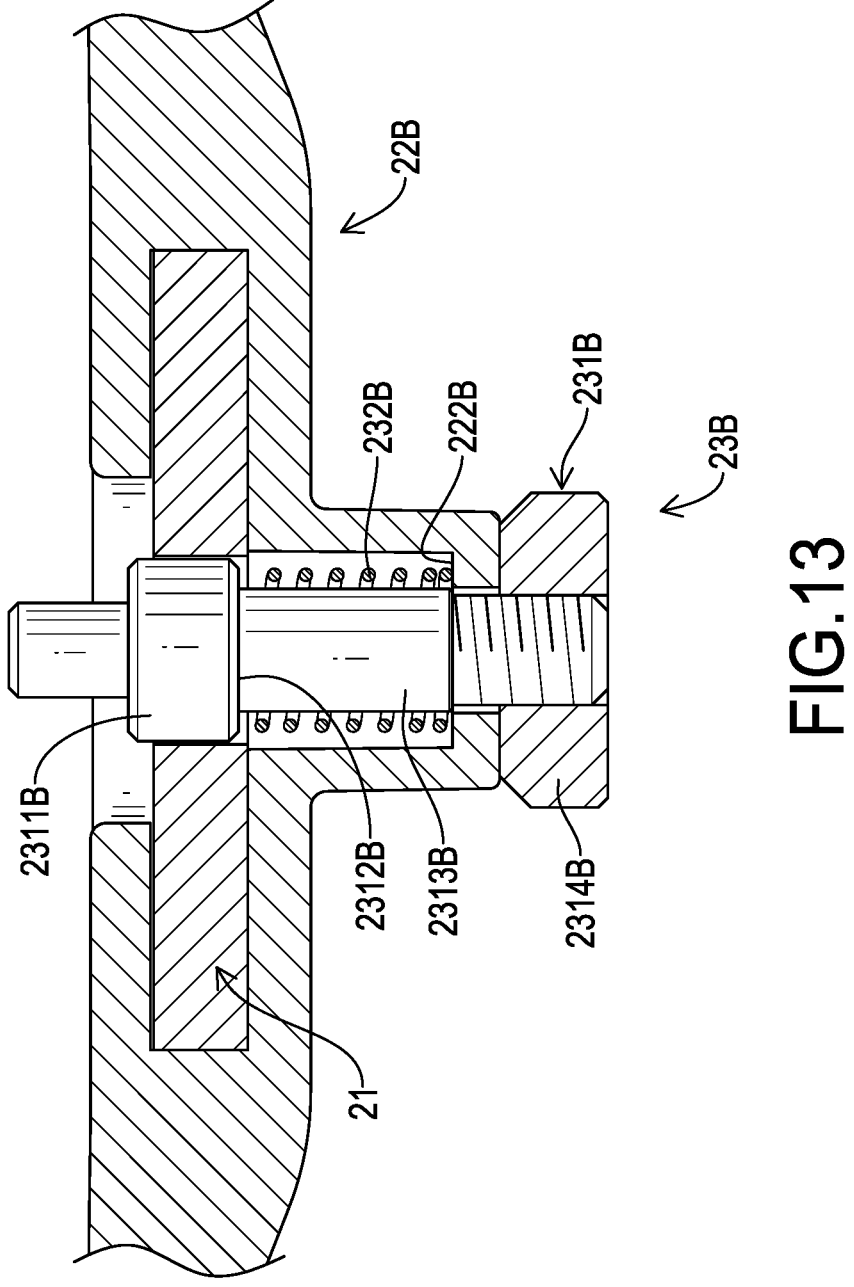
FIG. 13 is a cross-sectional view of the adjustable body brace in FIG. 11, showing the fixing module under the locked state.
Figure 14:
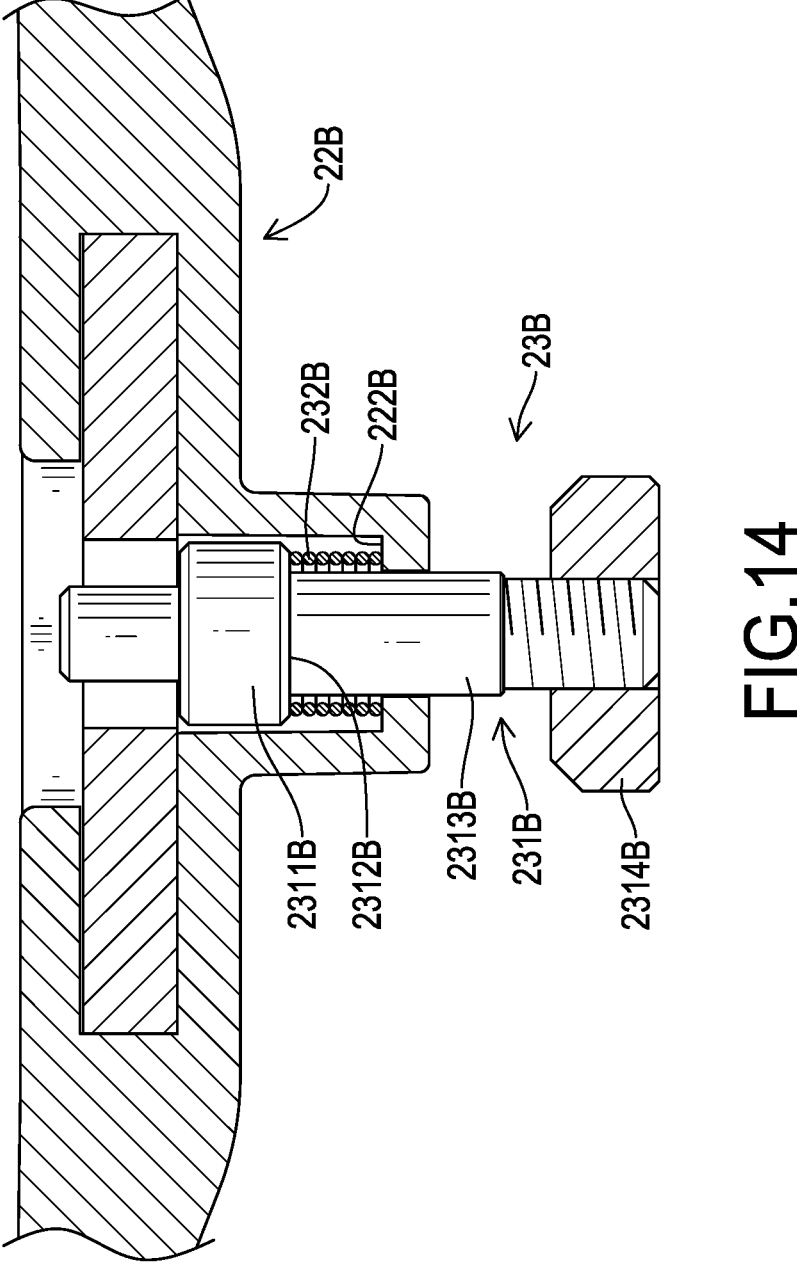
FIG. 14 is a cross-sectional view of the adjustable body brace in FIG. 11, shown the fixing module under the unlocked state.

To be more precise, the fixing module 23B in this embodiment is in a configuration of a pull-pin. As shown in FIG. 13, when the fixing module 23B is under the locked state, the engaging portion 2311B is located in the limit groove 213, the user is able to pull the engaging unit 231B via holding the handle 2314B, and thereby the second abutting surface 2312B moves toward the first abutting surface 222B, meanwhile, the second abutting surface 2312B compresses the elastic unit 232B; finally, the fixing module 23B is switched to the unlocked state as shown in FIG. 14, and the engaging portion 2311B is located out of the limit groove 213. When the user releases the handle 2314B, the elastic unit 232B stretches and pushes the engaging unit 231B to return to a position as shown in FIG. 13, thereby the fixing module 23B returns to the locked state, but it is not limited thereto; how the handle 2314B is connected with the extending portion 2313B may be altered, such that the fixing module 23B becomes a press-pin.

With the engaging unit 231 of the fixing module 23 engaged in different positions of the limit groove 213, the position of the slider 22 with respect to the base 21 is adjustable, and thereby a distance between the two board units 10 of the adjustable body brace is also adjustable to adjust the total length of the adjustable body brace. Therefore, positions on the user body supported by the adjustable body brace are changeable according to a body size or an injury status of the user, and the user does not need to endure the discomfort caused by improperly sized body brace, or spend extra money buying adjustable body braces in different sizes.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. An adjusting assembly comprising:
a base having a length direction and a thickness direction, and the base including:
a first surface;
a limit groove recessed from the first surface along the thickness direction and extending along the length direction; and
two wall surfaces respectively located on two opposite lateral sides of the limit groove, and each one of the two wall surfaces extending along the length direction;
a slider movably mounted on the base, and movable with respect to the base along the length direction;
a fixing module connected to the slider and mounted in the limit groove, and the fixing module having a locked state and an unlocked state; the fixing module including:
an engaging unit movable along the thickness direction and having:
an engaging portion selectively located in the limit groove;
wherein, when the fixing module is under the locked state, the engaging portion is in the limit groove and engages with the two wall surfaces, and thereby a position of the slider with respect to the base is fixed; when the fixing module is under the unlocked state, the engaging portion is out of the limit groove, thereby the slider being movable with respect to the base along the length direction;
wherein, the fixing module further includes an elastic unit connected to the engaging unit, and the elastic unit capable of driving the engaging unit to move along the thickness direction;
wherein, another surface opposite to the first surface of the base is a second surface, and the limit groove penetrates the second surface along the thickness direction; and
the elastic unit is connected to an end of the engaging unit, and the elastic unit is located out of the limit groove; the elastic unit further has at least one wing portion, the at least one wing portion abuts the second surface, thereby the engaging unit tending to move out from the limit groove;
wherein, the fixing module further includes a knob rotatably sleeved on the engaging unit and abutting the slider; the knob having:
an oblique surface located on a surface of the knob, and said surface away from the slider, and the oblique surface being oblique along a rotating direction of the knob;
an abutting unit connected to another end of the engaging unit, said end opposite to the elastic unit, and the abutting unit abutting the oblique surface and slidable with respect to the oblique surface; and an outer groove recessed from an outer annular surface of the knob, and the outer groove extending along a circumferential direction of the knob and having two opposite ends;
the slider further has a protrusion located in the outer groove; and
when the fixing module is under the locked state or the unlocked state, the protrusion is located at either one of the two opposite ends of the outer groove.

2. The adjusting assembly as claimed in claim 1, wherein:
the limit groove further has:
multiple limit segments disposed along the length direction and spaced apart from each other; and
multiple connecting segments, each one of the connecting segments connecting each adjacent two of the limit segments;
a distance between the two wall surfaces at each one of the limit segments is a first width, another distance between the two wall surfaces at each one of the connecting segments is a second width, and the first width is larger than the second width; and
a width of the engaging portion is smaller than or equal to the first width, and the width of the engaging portion is larger than the second width.

3. An adjustable body brace comprising:
an adjusting assembly having:
a base having a length direction and a thickness direction, and the base including:
a first surface;
a limit groove recessed from the first surface along the thickness direction and extending along the length direction; and
two wall surfaces respectively located on two opposite lateral sides of the limit groove, and each one of the two wall surfaces extending along the length direction;
a slider movably mounted on the base, and movable with respect to the base along the length direction;
a fixing module connected to the slider and mounted in the limit groove, and the fixing module having a locked state and an unlocked state; the fixing module including:
an engaging unit movable along the thickness direction and having:
an engaging portion selectively located in the limit groove;
wherein, when the fixing module is under the locked state, the engaging portion is in the limit groove and engages with the two wall surfaces, and thereby a position of the slider with respect to the base is fixed; when the fixing module is under the unlocked state, the engaging portion is out of the limit groove, thereby the slider being movable with respect to the base along the length direction;
wherein, the fixing module further includes an elastic unit connected to the engaging unit, and the elastic unit capable of driving the engaging unit to move along the thickness direction;
wherein, another surface opposite to the first surface of the base is a second surface, and the limit groove penetrates the second surface along the thickness direction; and
the elastic unit is connected to an end of the engaging unit, and the elastic unit is located out of the limit groove; the elastic unit further has at least one wing portion, the at least one wing portion abuts the second surface, thereby the engaging unit tending to move out from the limit groove;

wherein, the fixing module further includes a knob rotatably sleeved on the engaging unit and abutting the slider; the knob having:

an oblique surface located on a surface of the knob, and said surface away from the slider, and the oblique surface being oblique along a rotating direction of the knob;

an abutting unit connected to another end of the engaging unit, said end opposite to the elastic unit, and the abutting unit abutting the oblique surface and slidable with respect to the oblique surface; and an outer groove recessed from an outer annular surface of the knob, and the outer groove extending along a circumferential direction of the knob and having two opposite ends;

the slider further has a protrusion located in the outer groove; and when the fixing module is under the locked state or the unlocked state, the protrusion is located at either one of the two opposite ends of the outer groove; and two board units respectively connected to the base and the slider.

4. The adjustable body brace as claimed in claim 3, wherein, the adjustable body brace further includes multiple belts, and each one of the board units has:

multiple penetrating holes formed through the board unit, and each one of the belts mounted in the penetrating holes.

\* \* \* \* \*